(12) United States Patent
Tsai et al.

(10) Patent No.: US 11,361,783 B2
(45) Date of Patent: Jun. 14, 2022

(54) COMPUTER-AIDED CONVERSION TEST SYSTEM AND METHOD FOR GENERATING INTELLIGIBLE SPEECH

(71) Applicant: TS Voice Technology, LLC, Oakland, CA (US)

(72) Inventors: Shu-Wei Tsai, Oakland, CA (US); Heng-chin Yeh, Oakland, CA (US); Yi-Hsin Chen, Oakland, CA (US)

(73) Assignee: TS VOICE TECHNOLOGY, LLC, Oakland, CA (US)

( * ) Notice: Subject to any disclaimer, the term of this patent is extended or adjusted under 35 U.S.C. 154(b) by 284 days.

(21) Appl. No.: 16/740,890

(22) Filed: Jan. 13, 2020

(65) Prior Publication Data
US 2020/0227072 A1    Jul. 16, 2020

Related U.S. Application Data

(60) Provisional application No. 62/792,932, filed on Jan. 16, 2019.

(51) Int. Cl.
| | |
|---|---|
| *G10L 13/02* | (2013.01) |
| *G10L 25/66* | (2013.01) |
| *G10L 15/16* | (2006.01) |
| *G10L 15/22* | (2006.01) |
| *G10L 15/06* | (2013.01) |
| *G06F 3/16* | (2006.01) |
| *G06N 20/00* | (2019.01) |

(52) U.S. Cl.
CPC .............. *G10L 25/66* (2013.01); *G06F 3/167* (2013.01); *G06N 20/00* (2019.01); *G10L 15/063* (2013.01); *G10L 15/16* (2013.01); *G10L 15/22* (2013.01)

(58) Field of Classification Search
CPC ....... G10L 13/02; G10L 13/00; G10L 13/027; G10L 13/033; G10L 13/04; G10L 13/047
USPC .......................... 704/258, 259, 261, 266, 268
See application file for complete search history.

(56) References Cited

U.S. PATENT DOCUMENTS

| | | | | |
|---|---|---|---|---|
| 4,586,931 A | * | 5/1986 | Blom | ........................ A61F 4/00 623/9 |
| 5,828,758 A | * | 10/1998 | Byce | ...................... G09B 21/00 381/70 |
| 6,006,175 A | * | 12/1999 | Holzrichter | .......... A61B 5/0507 704/205 |

(Continued)

*Primary Examiner* — Qi Han
(74) *Attorney, Agent, or Firm* — Muncy, Geissler, Olds & Lowe, P.C.

(57) ABSTRACT

The present invention provides a computer-aided conversion test system and method for generating intelligible speech. The test system includes an acoustic test module with a nasal-genio-oropharyngeal tract, a transmitting module generates a detecting signal, a first receiving module, a second receiving module, and a central processing module with a plurality of first phonetically oral cavity shape spectra. By adjusting the transmitting module, the first receiving module, or the second receiving module, a second phonetically oral cavity shape spectrum is correctly compared and identified by a central computing unit as one of the corresponding first phonetically oral cavity shape spectra. After testing, training and adjusting through the test method, the detecting signal transmitted by the transmitting module is analyzed and identified by the central processing module to increase its interpretation accuracy and shorten the time of machine learning.

10 Claims, 8 Drawing Sheets

(56) References Cited

U.S. PATENT DOCUMENTS 9,143,106 B1* 9/2015 Grocela .................. G10L 13/04
2012/0150544 A1* 6/2012 McLoughlin ....... G10L 21/0364
704/262

* cited by examiner

| artificial neural network classification | phoneme | accuracy |
|---|---|---|
| vowel | a, e, i, o, u | 99.7% |
| consonant | P, t, l, s, k | 90.3% |
| syllable | pa, ta, la, sa, ka | 92.6% |
| consonant+syllable | P, t, l, s, k, pa, ta, la, sa, ka | 81.8% |
| vowel+consonant+syllable | a, e, i, o, u, p, t, l, s, k, pa, ta, la, sa, ka | 85.3% |

COMPUTER-AIDED CONVERSION TEST SYSTEM AND METHOD FOR GENERATING INTELLIGIBLE SPEECH

FIELD OF THE INVENTION

The present invention relates to a computer-aided conversion test system and method for generating intelligible speech, and more particularly to a computer-aided conversion test system and method for generating intelligible speech that uses an acoustic test module with an imitated nasal-genio-oropharyngeal tract capable of testing patients whose vocal cord cannot vocalize.

BACKGROUND OF THE INVENTION

Laryngeal cancer is a common cause of dysfunction of vocalization. Patients having laryngeal cancer lose their natural ability to vocalize after undergoing a total laryngectomy. In order to overcome the troubles with the vocalization of such patients, one of the previous solutions provides detecting electrodes on the surfaces of the patient's head and neck to detect the intention in the speaking of the patient according to changes in the head and the neck. Another solution, the technique of permanent-magnetic articulography, is to connect magnets to the patient's tongue and lips and infer the patient's speech by learning the patient's intraoral motion according to changes of the magnetic field.

Figure 1:
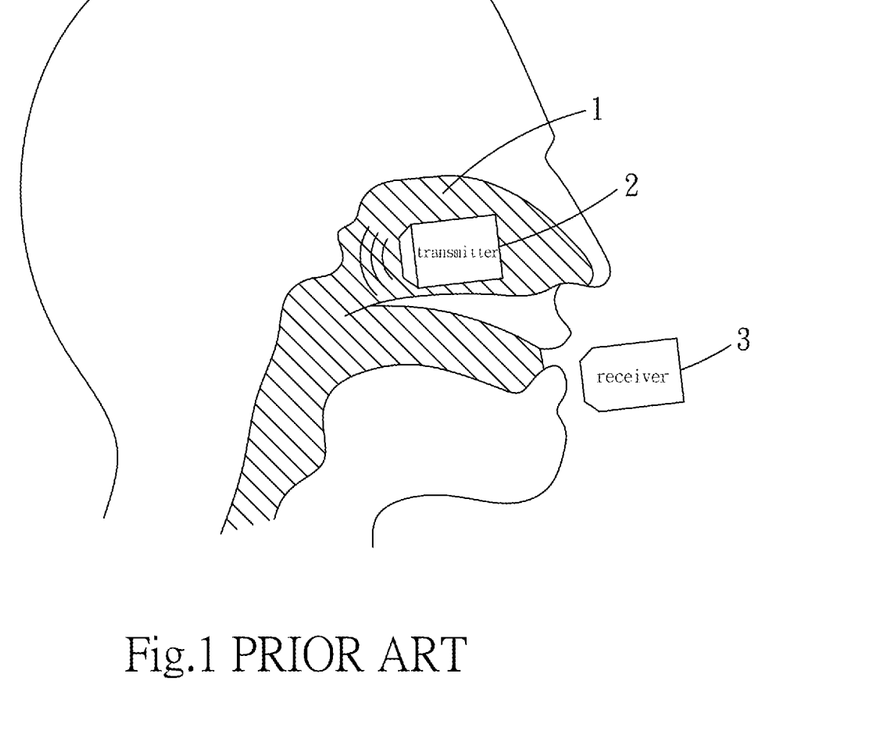
FIG. 1 is a schematic diagram of a user disposed with a computer-aided conversion device for generating intelligible speech.

However, the aforementioned detection method requires disposing the detecting electrodes directly on the patient's head, or the technique of permanent-magnetic articulography requires to dispose many sensors on the patient's tongue and lips, as that the data processing speed is slow and the detection devices are difficult to be realized in the portable form. Please refer to FIG. 1, which is a computer-aided conversion device for generating intelligible speech disclosed in U.S. Provisional Application No. 62/595,013. A transmitter 2 is disposed in a nasal cavity 1 of a patient, and a receiver 3 is disposed in front of the lips. The computer-aided conversion device for generating intelligible speech can find out what is the speech expressed by a patient by using the receiver 3 to collect a detecting signal sent out by the transmitter 2 and using a computation unit to analyze and determine the detecting signal resonated by the nasal cavity 1 before receiving by the receiver 3.

Accordingly, it is difficult to accurately convert the speech that the patient wants to express through above-mentioned computer-aided conversion device which is tested, trained, and adjusted before the user operates the device. Therefore, how to overcome the drawbacks of the previous technique is an important issue.

SUMMARY OF THE INVENTION

An object of the present invention is to provide a computer-aided conversion test system and method for generating intelligible speech capable of testing, training, and adjusting the technique of the prior art.

In order to achieve the above object, the present invention provides a computer-aided conversion test system for generating intelligible speech comprising: an acoustic test module, a transmitting module, a first receiving module and a central processing module. The acoustic test module includes a nasal-genio-oropharyngeal tract including a nasal cavity unit with two first openings communicating with external environment, an oral cavity unit with a second opening communicating with external environment, a pharyngeal unit connecting the nasal cavity unit and the oral cavity unit, and a laryngeal unit abutting another end of the pharyngeal unit; the transmitting module is disposed at one of the first openings of the nasal cavity unit; the first receiving module is disposed at the second opening of the oral cavity unit; and the central processing module includes a transmitting-computing unit configured to control the transmitting module to generate a detecting signal, a receiving-computing unit configured to analyze the detecting signal received by the first receiving module, a database storing a plurality of first phonetically oral cavity shape spectra, and a central computing unit configured to perform machine learning; wherein the central computing unit is electrically connected to the transmitting-computing unit, the receiving-computing unit and the database, and through the receiving-computing unit converts the detecting signal passing through the nasal-genio-oropharyngeal tract and received by the first receiving module into a second spectrum corresponding to an acoustic model of an articulatory cavity; the central computing unit analyzes and compares the second phonetically oral cavity shape spectrum converted by the receiving-computing unit and the first phonetically oral cavity shape spectra in the database; and by adjusting the transmitting module or the first receiving module, the central computing unit is capable of correctly comparing and identifying one of the first phonetically oral cavity spectra stored in the database corresponding to and according to the second phonetically oral cavity spectrum after the detecting signal generated by the transmitting module is received by the first receiving module.

Further, a third opening is disposed at another end of the laryngeal unit opposite to the end abutting the pharyngeal unit, and the third opening is disposed with a second receiving module connected to the receiving-computing unit.

Further, by adjusting the second receiving module, the central computing unit is capable of correctly comparing and identifying one of the first phonetically oral cavity spectra stored in the database corresponding to and according to the second phonetically oral cavity spectrum after the detecting signal generated by the transmitting module is received by the second receiving module.

Further, the first receiving module is disposed at a position within 3 cm in front of the second opening of the oral cavity unit.

Further, the detecting signal is configured as a sound wave ranged from 16 Hz to 22 KHz.

Further, another object of the present invention is to provide a computer-aided conversion test method for generating intelligible speech comprising following steps of: step S1: providing an acoustic test module with a nasal-genio-oropharyngeal tract, the nasal-genio-oropharyngeal tract including a nasal cavity unit with two first openings communicating with external environment, an oral cavity unit with a second opening communicating with external environment, a pharyngeal unit connecting the nasal cavity unit and the oral cavity unit, and a laryngeal unit abutting another end of the pharyngeal unit; step S2: providing a central processing module, the central processing module including a transmitting-computing unit, a receiving-computing unit, a database storing a plurality of first phonetically oral cavity shape spectra, and a central computing unit configured to perform machine learning; step S3: disposing a transmitting module at one of the first openings of the nasal cavity unit and a first receiving module at the second opening of the oral cavity unit respectively; step S4: generating a detecting signal by the transmitting module which is controlled by the transmitting-computing unit, and receiving the detecting signal reflected by the nasal-genio-oropharyngeal tract by the first receiving module; step S5: converting the detecting signal received by the first receiving module into a second phonetically oral cavity shape spectrum by the receiving-computing unit; step S6: analyzing the first phonetically oral cavity shape spectra and the second phonetically oral cavity shape spectrum by the central computing unit; and step S7: determining whether the transmitting module or the first receiving module require being adjusted, if the central computing unit being capable of correctly comparing and identifying one of the first phonetically oral cavity shape spectra stored in the database which corresponds to the second phonetically oral cavity shape spectrum, no adjustment being required, contrarily, after adjusting, performing from step 4 again and adjusting until capable of being identified.

Further, step S3 further includes disposing a second receiving module at a third opening at another end of the laryngeal unit opposite to the end abutting the pharyngeal unit.

Further, step S7 further includes adjusting the first receiving module so that the central computing unit is capable of correctly comparing and identifying one of the first phonetically oral cavity shape spectra stored in the database which corresponds to the second phonetically oral cavity shape spectrum.

Further, in step S3, the first receiving module is disposed at a position within 3 cm in front of the second opening of the oral cavity unit.

Further, the detecting signal generated in step S4 is configured as a sound wave ranged from 16 Hz to 22 KHz.

Therefore, the test system of the present invention disposes the transmitting module in the nasal cavity opening of the acoustic test module with the imitated nasal-genio-oropharyngeal tract, so that after the first receiving module provided in the oral cavity unit or the second receiving module provided in the laryngeal unit are tested, trained, and adjusted, the vowels, consonants, syllables and their combinations sent out by the transmitting module can be analyzed and identified by the first receiving module, the second receiving module, or their combination, thereby increasing their interpretation accuracy and shortening the time of machine learning. The test method of the present invention is to test, train, and adjust the transmitting module, the first receiving module and the second receiving module by using the acoustic test module with the imitated nasal-genio-oropharyngeal tract, so that after the detecting signal sent by the transmitting module passes through the nasal-genio-oropharyngeal tract and is received by the first receiving module and the second receiving module, the central computing unit is capable of correctly comparing and identifying one of the first phonetically oral cavity shape spectra stored in the database which corresponds to the second phonetically oral cavity shape spectrum, thereby the advantages of real-time operation and interpretation are achieved after a user is disposed with the present invention.

DETAILED DESCRIPTION OF THE PREFERRED EMBODIMENTS

The technical contents, features and efficacies of the present invention will be clearly presented in the following detailed description of the preferred embodiments with reference to the accompanying drawings.

Figure 2:
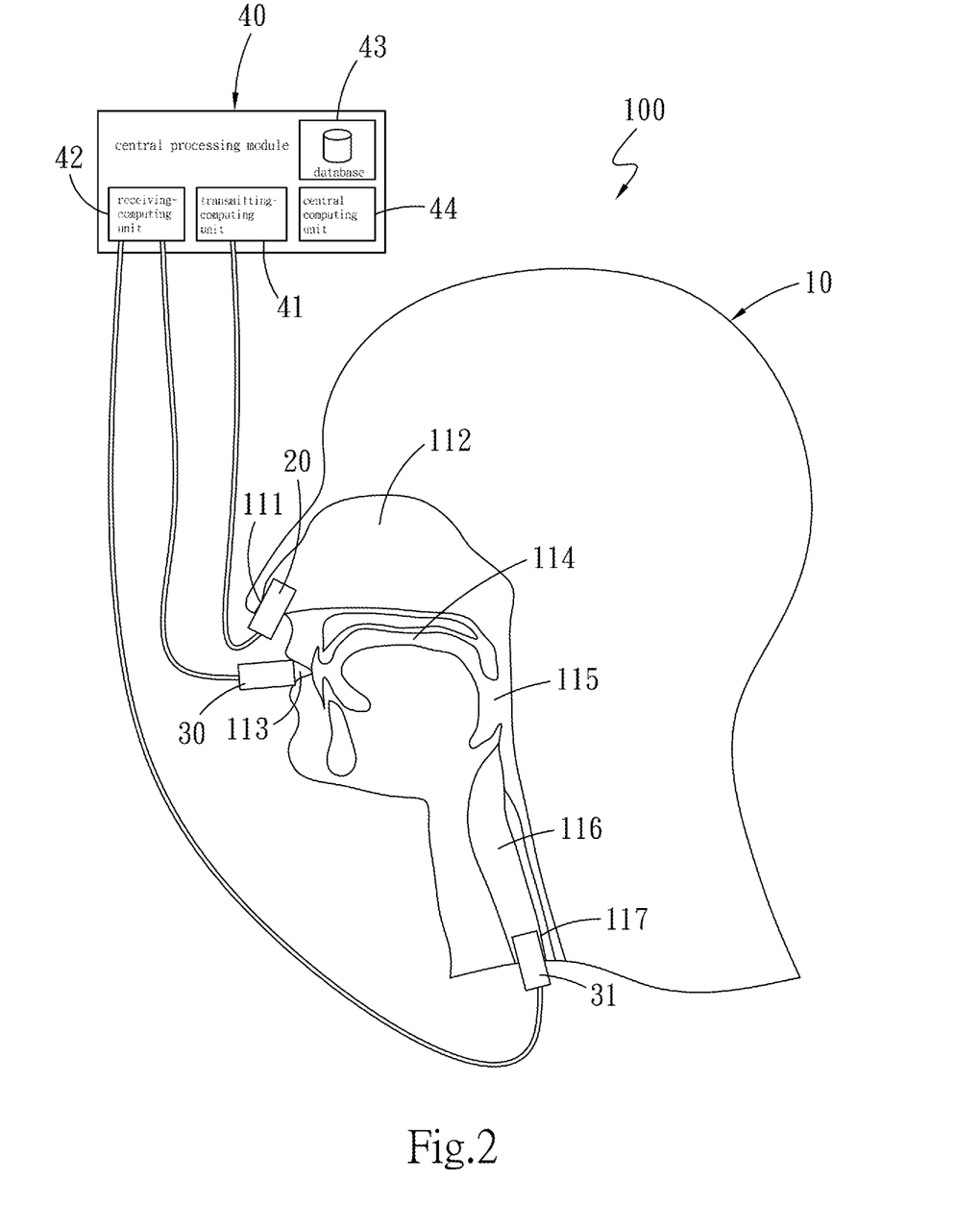
FIG. 2 is a schematic diagram of using a test system of a first embodiment of the present invention.

Please refer to FIG. 2. The present invention provides a computer-aided conversion test system for generating intelligible speech 100 capable of testing, training, and adjusting a computer-aided conversion device for generating intelligible speech 100 used by a speech not originated from a vocal cord of a user. The above-mentioned "speech not originated from the vocal cord of the user" means that the user cannot perfectly speak as a normal person due to factors such as throat disease or injury, but when the user attempts to speak, the computer-aided conversion device for generating intelligible speech 100 is capable of inferring the original intention in the speaking of the user. For specific description, please refer to FIG. 2 and FIG. 3, the computer-aided conversion test system for generating intelligible speech 100 includes an acoustic test module 10, a transmitting module 20, a first receiving module 30 and a central processing module 40.

Figure 3:
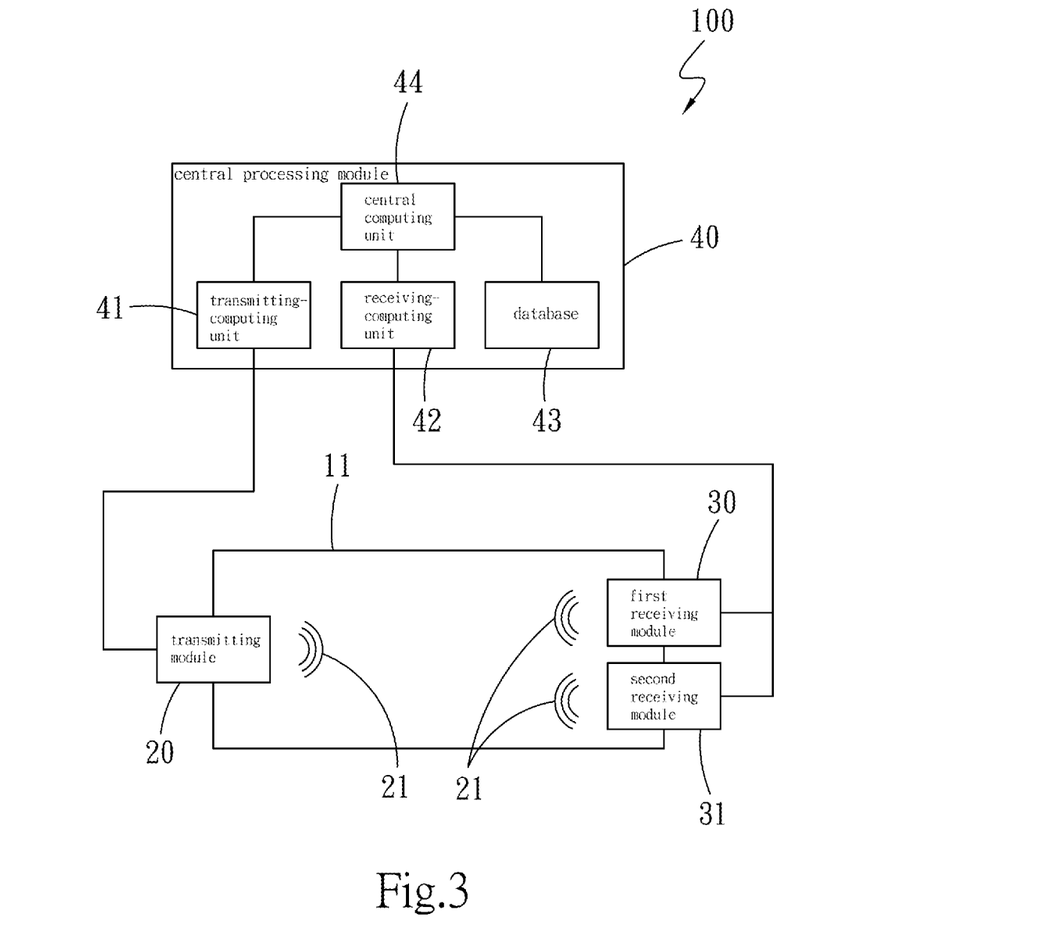
FIG. 3 is a block diagram of the test system of the first embodiment of the present invention.

The acoustic test module 10 includes a nasal-genio-oropharyngeal tract 11 (shown in FIG. 3). In detail, the nasal-genio-oropharyngeal tract 11 includes a nasal cavity unit 112 with two first openings 111 which communicate with external environment (FIG. 2 shows only one of the first openings 111), an oral cavity unit 114 with a second opening 113 which communicates with external environment, a pharyngeal unit 115 with one end connecting the nasal cavity unit 112 and the oral cavity unit 114, and a laryngeal unit 116 abutting another end of the pharyngeal unit 115. A third opening 117 is disposed at another end of the laryngeal unit 116 opposite to the end abutting the pharyngeal unit 115. In a first embodiment of the present invention, the acoustic test module 10 is designed according to the nasal-genio-oropharyngeal tract 11 of the user.

The transmitting module 20 is disposed at one of the first openings 111 of the nasal cavity unit 112, and the other first opening 111 not disposed with the transmitting module 20 is in an opened state or a closed state. In another embodiment, both of the two first openings 111 are provided with the transmitting modules 20.

The first receiving module 30 is disposed at the second opening 113 of the oral cavity unit 114. The first embodiment of the present invention further provides a second receiving module 31 at the third opening 117 of the laryngeal unit 116, and the first receiving module 30 is disposed at a position within 3 cm in front of the second opening 113 of the oral cavity unit 114, but is not limited thereto.

The central processing module 40 includes a transmitting-computing unit 41 configured to control the transmitting module 20 to generate a detecting signal 21 (shown in FIG. 3), a receiving-computing unit 42 configured to analyze the detecting signal 21 received by the first receiving module 30, the second receiving module 31 or the combination thereof, a database 43 storing a plurality of first phonetically oral cavity shape spectra, and a central computing unit 44 configured to perform machine learning. The central computing unit 44 is electrically connected to the transmitting-computing unit 41, the receiving-computing unit 42 and the database 43. The receiving-computing unit 42 converts the detecting signal 21, which passes through the nasal-genio-oropharyngeal tract 11 and is received by the first receiving module 30 and the second receiving module 31, into a second phonetically oral cavity shape spectrum. The detecting signal 21 is configured as a sound wave ranged from 16 Hz to 22 KHz. In one embodiment, the detecting signal 21 is further configured as a sound wave ranged from 20 Hz to 20 KHz. The detecting signal 21 may also be transmitted in waveform such as ultrasonic wave, electromagnetic wave, visible or invisible light wave, etc. The machine learning described above may be an artificial neural network (ANN), but is not limited thereto.

The central computing unit 44 analyzes and compares the second phonetically oral cavity shape spectrum converted by the receiving-computing unit 42 and the first phonetically oral cavity shape spectra stored in the database 43. By adjusting the spectrum parameters of an audio transmitted by the transmitting module 20, the audio received by the first receiving module 30 or the audio received by the second receiving module 31, the central computing unit 44 is capable of correctly comparing and identifying one of the first phonetically oral cavity spectra stored in the database 43 which corresponds to the second phonetically oral cavity shape spectrum after the detecting signal 21 generated by the transmitting module 20 is received by the first receiving module 30, the second receiving module 31 or their combination.

Figure 4:
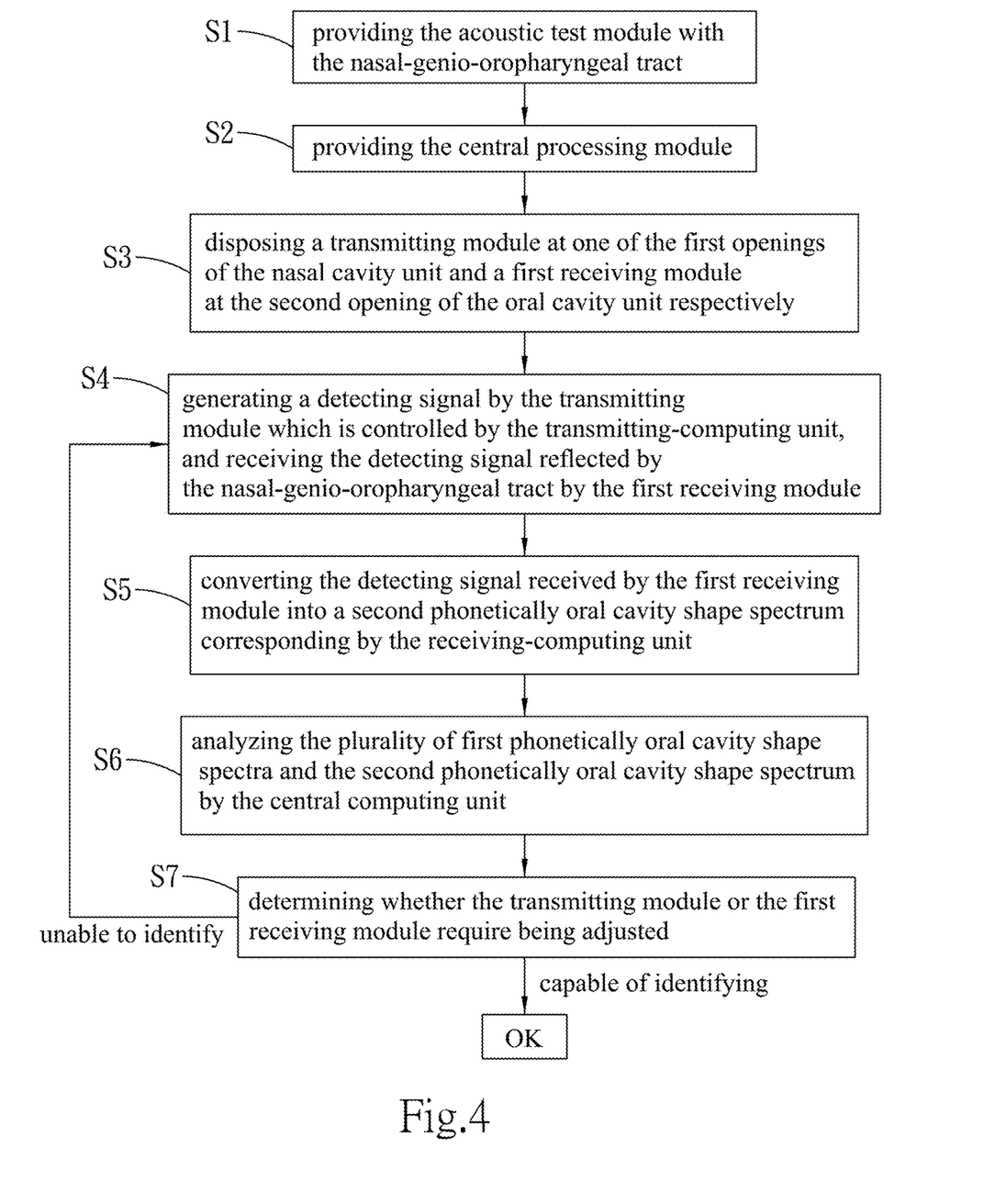
FIG. 4 is a flowchart of a test method of the first embodiment of the present invention.

Please refer to FIG. 4, a computer-aided conversion test method for generating intelligible speech 100 is described as follow. The computer-aided conversion test method of the invention is capable of increasing the accuracy of correct interpretation when the user utilizes the computer-aided conversion device for generating intelligible speech 100 at the beginning even though the phonetically oral cavity shape of each user comprises its specificity. The computer-aided conversion test method includes the following steps of:

step S1: providing the acoustic test module 10 with the nasal-genio-oropharyngeal tract 11;

step S2: providing the central processing module 40;

step S3: disposing the transmitting module 20 at one of the first openings 111 of the nasal cavity unit 112, disposing the first receiving module 30 at the second opening 113 of the oral cavity unit 114, and disposing the second receiving module 31 at the third opening 117 of the laryngeal unit 116, wherein in the first embodiment of the present invention, the first receiving module 30 is disposed at a position within 3 cm in front of the second opening 113 of the oral cavity unit 114, but is not limited thereto;

step S4: generating the detecting signal 21 by the transmitting module 20 which is controlled by the transmitting-computing unit 41, receiving the detecting signal 21 reflected by the nasal cavity unit 112, the pharyngeal unit 115, the laryngeal unit 116 and the oral cavity unit 114 of the nasal-genio-oropharyngeal tract 11 by the first receiving module 30, the second receiving module 31 or the combination thereof, and configuring the detecting signal 21 as a sound wave from 16 Hz to 22 KHz. In one embodiment, the detecting signal 21 is further configured as a sound wave from 20 Hz to 20 KHz, but is not limited thereto;

step S5: converting the detecting signal 21 received by the first receiving module 30 and the second receiving module 31 into the second phonetically oral cavity shape spectrum by the receiving-computing unit 42;

step S6: analyzing the first phonetically oral cavity shape spectra and the second phonetically oral cavity shape spectrum by the central computing unit 44; and step S7: determining whether the transmitting module 20, the first receiving module 30 or the second receiving module 31 require being adjusted. If the central computing unit 44 is capable of correctly comparing and identifying one of the first phonetically oral cavity shape spectra stored in the database 43 which corresponds to the second phonetically oral cavity shape spectrum, no adjustment being required; contrarily, after adjusting, performing from step 4 again sequentially.

Figure 5:
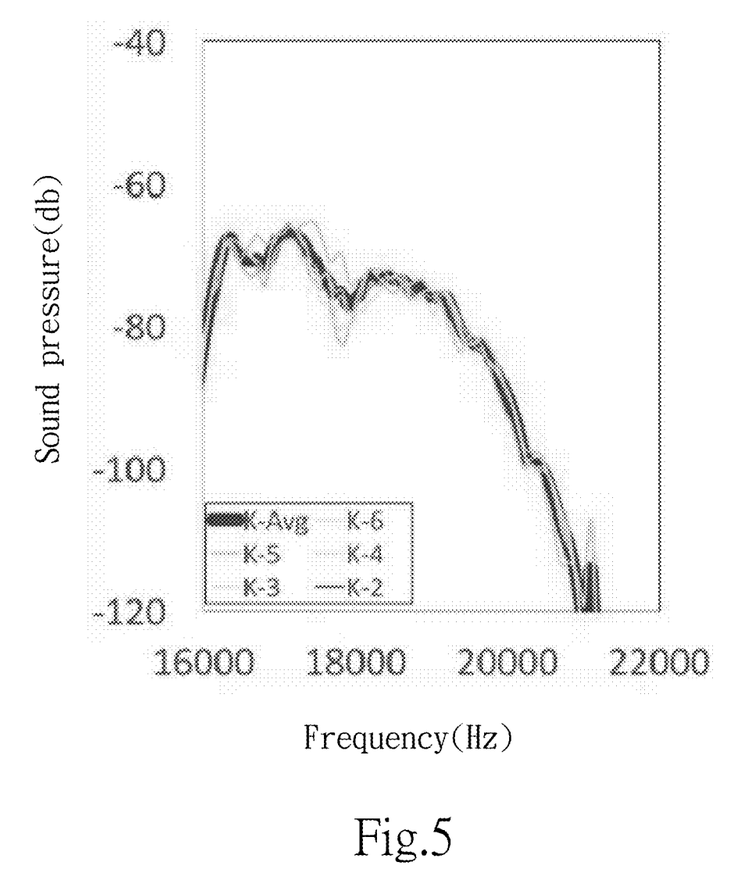
FIG. 5 is a graph of a spectrum corresponding to an acoustic model of an articulatory cavity of the present invention corresponding to a pronunciation of "K" by the user.

Please refer to FIG. 5, the transmitting-computing unit 41 controls the transmitting module 20 to generate the detecting signal 21 for a "K" sound, and the detecting signal 21 is collected by the first receiving module 30 and the second receiving module 31. After multiple times of collection, the detecting signals 21 are converted into the second phonetically oral cavity shape spectra by the receiving-computing unit 42, and the average value of the second phonetically oral cavity shape spectra is obtained (that is, the thicker line K-Avg in FIG. 5). Then, the average values of the second phonetically oral cavity shape spectra are calculated by the central computing unit 44 and compared with the first phonetically oral cavity shape spectra stored in the database 43. Accordingly, it can be known whether the average value of the second phonetically oral cavity shape spectra, which are converted by the receiving-computing unit 42 from the sound wave received by the first receiving module 30 or the second receiving module 31, are corresponded to a "K" sound stored in the first phonetically oral cavity shape spectrum. If it is not the "K" sound, the spectrum parameters of the audio received by the first receiving module 30 and the second receiving module 31 can be adjusted to make the average value of the second phonetically oral cavity shape spectrum approximately corresponds with the "K" sound of the first phonetically oral cavity shape spectrum. Besides, the transmitting module 20 can also be adjusted to make a "K" sound generated by the transmitting module 20, and the "K" sound is received by the first receiving module 30 and the second receiving module 31 and converted via the receiving-computing unit 42 into the second phonetically oral cavity shape spectrum, causing the average value of the second phonetically oral cavity shape spectrum approximately corresponds with the "K" sound stored in the first phonetically oral cavity shape spectrum.

Figure 6:
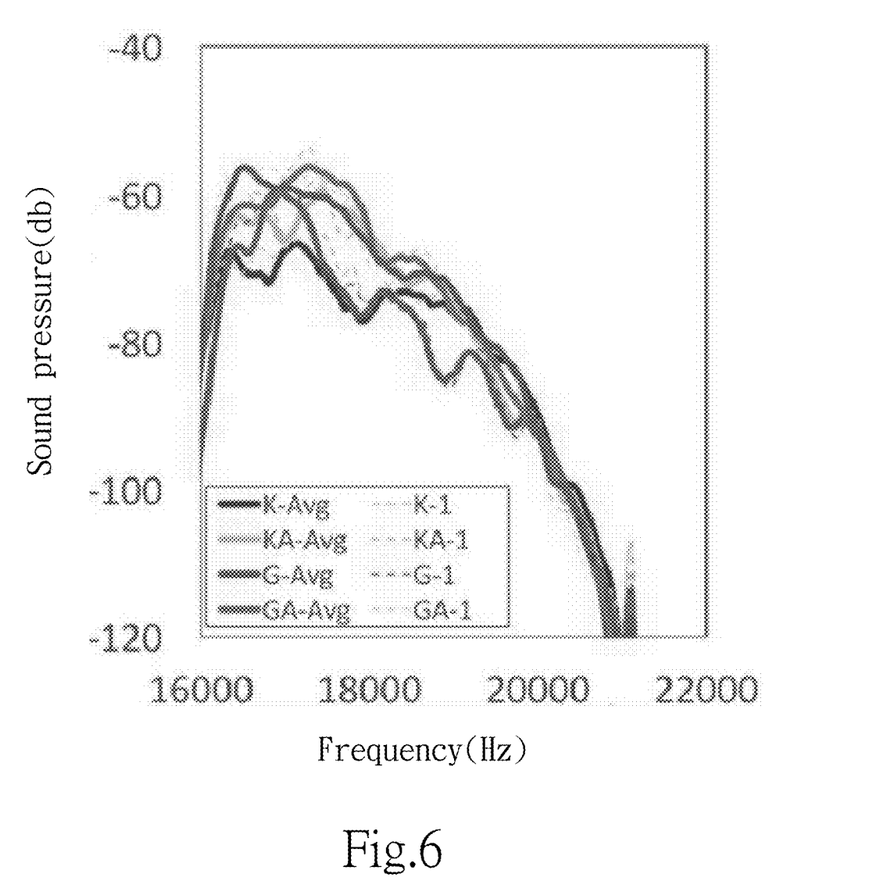
FIG. 6 is a graph of a spectrum corresponding to an acoustic model of an articulatory cavity of the present invention corresponding to pronunciations of "K", "KA", "G", and "GA" by the user.

Please refer to FIG. 6, the transmitting-computing unit 41 controls the transmitting module 20 to generate the detecting signals 21 for sounds of "K", "KA", "G", "GA", and after the detecting signals 21 are collected by the first receiving module 30 and the second receiving module 31 multiple times and converted into the second phonetically oral cavity shape spectra by the receiving-computing unit 42, the average values of the second phonetically oral cavity shape spectra of the four sounds are obtained. Then, the average values of the second phonetically oral cavity shape spectra are calculated by the central computing unit 44 and compared with the first phonetically oral cavity shape spectra stored in the database 43. Accordingly, it can be known whether the average value of the second phonetically oral cavity shape spectra, which are converted by the receiving-computing unit 42 from the sound wave received by the first receiving module 30 or the second receiving module 31, are corresponded to "K", "KA", "G", "GA" sound of the first phonetically oral cavity shape spectra. If they are not the "K", "KA", "G", "GA" sounds, the spectrum parameters of the audio received by the first receiving module 30 and the second receiving module 31 can be adjusted to make the average value of the second phonetically oral cavity shape spectrum approximately corresponds with the "K", "KA", "G", "GA" sounds of the first phonetically oral cavity shape spectra. Besides, the transmitting module 20 can also be adjusted to make the "K", "KA", "G", "GA" sounds generated by the transmitting module 20, and the "K", "KA", "G", "GA" sounds are received by the first receiving module 30 and the second receiving module 31 and converted via the receiving-computing unit 42 into the second phonetically oral cavity shape spectrums approximately corresponds with the "K", "KA", "G", "GA" sounds of the first phonetically oral cavity shape spectra.

Figure 7:
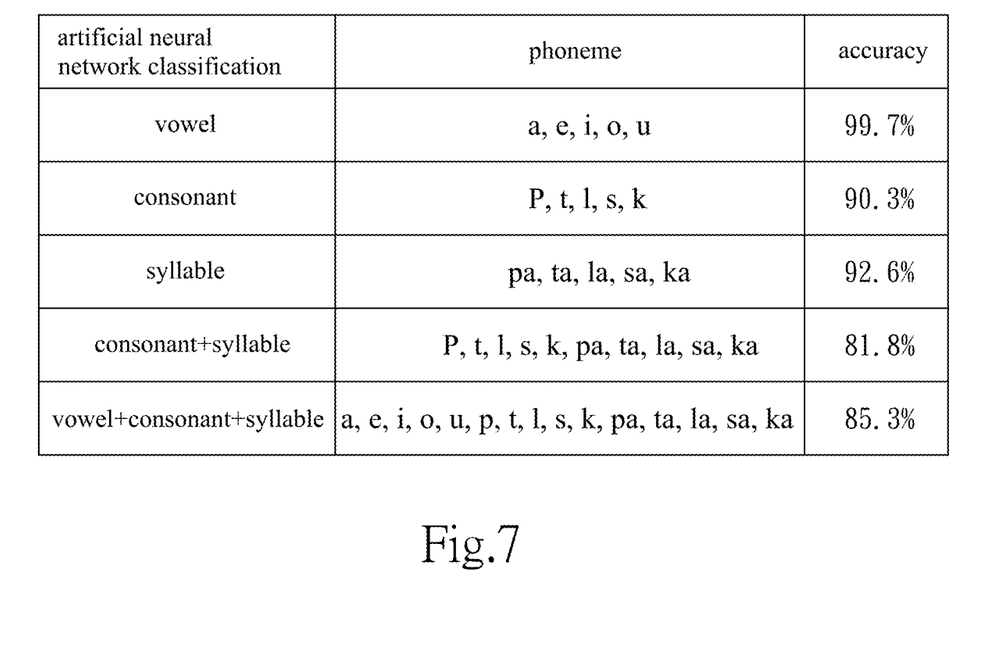
FIG. 7 is an accuracy comparison of the computer-aided conversion device for generating intelligible speech after testing by the test system of the present invention.

Please refer to FIG. 7. The computer-aided conversion device for generating intelligible speech corrected by the test system and method of the first embodiment of the present invention is further tried out by the user attempting to pronounce various vowels and consonants, and a combined pronunciation of continuous syllables of the vowels and consonants. After repeated experiments, the accuracy of distinguishing the vowels, consonants, syllables and their combinations is higher than 81.8%. After the computer-aided conversion device for generating intelligible speech employs the test system and method, not only has a high degree of reliability in interpreting the speech intention of a person with speech dysfunction, but is also capable of shortening machine learning time for the computer-aided conversion device for generating intelligible speech.

Figure 8:
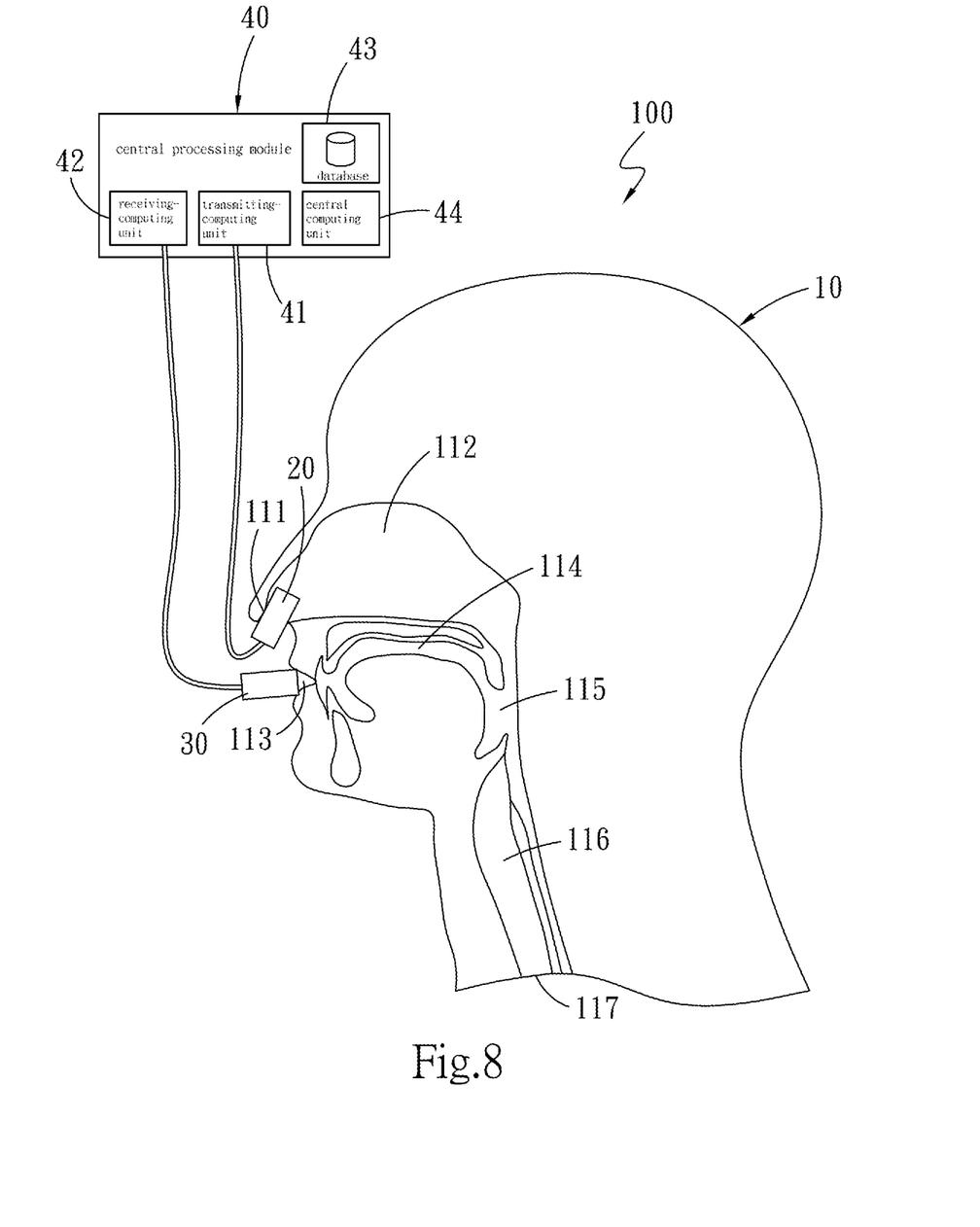
FIG. 8 is a schematic diagram of using the test system of a second embodiment of the present invention.

Please refer to FIG. 8, which refers to the test system of a second embodiment of the present invention. The main features that are the same as those of the first embodiment will not be described again. The difference is that the third opening 117 of the oral cavity unit 114 is no longer disposed with the second receiving module 31. Therefore, the receiving-computing unit 42 only needs to convert the detecting signal 21 received by the first receiving module 30 and convert the detecting signal 21 into the second spectrum, and the rest of the adjustments and test method are the same as those of the first embodiment.

Therefore, the features of the present invention and the expected efficacies that can be achieved are stated as follows:

The computer-aided conversion test system and method for generating intelligible speech of the present invention dispose the transmitting module 20 at the first opening 111 of the nasal cavity unit 112 of the acoustic test module 10 with the imitated nasal-genio-oropharyngeal tract 11, and the transmitting module 20 generates the detecting signal 21, so that the detecting signal 21 is reflected by the nasal-genio-oropharyngeal tract 11. After the first receiving module 30 disposed at the second opening 113 of the oral cavity unit 114, or the second receiving module 31 disposed at the the third opening 117 of the laryngeal unit 116 are tested, trained, and adjusted, the detecting signal 21 of the vowels, consonants, syllables and their combinations generated by the transmitting module 20 can be analyzed by the first receiving module 30, the second receiving module 31, or their combination, and identified by the central processing module 40, thereby increasing their interpretation accuracy and shortening the time of machine learning.

What is claimed is:

1. A computer-aided conversion test system for generating intelligible speech, comprising:
    an acoustic test module including a nasal-genio-oropharyngeal tract including a nasal cavity unit with two first openings communicating with external environment, an oral cavity unit with a second opening communicating with external environment, a pharyngeal unit with one end connecting the nasal cavity unit and the oral cavity unit, and a laryngeal unit abutting another end of the pharyngeal unit;
    a transmitting module disposed at one of the first openings of the nasal cavity unit;
    a first receiving module disposed at the second opening of the oral cavity unit; and
    a central processing module including a transmitting-computing unit configured to control the transmitting module to generate a detecting signal, a receiving-computing unit configured to analyze the detecting signal received by the first receiving module, a database storing a plurality of first phonetically oral cavity shape spectra, and a central computing unit configured to perform machine learning, wherein the central computing unit is electrically connected to the transmitting-computing unit, the receiving-computing unit and the database, and the receiving-computing unit converts the detecting signal, which passes through the nasal-genio-oropharyngeal tract and is received by the first receiving module, into a second phonetically oral cavity shape spectrum corresponding to an acoustic model of an articulatory cavity;
    wherein the central computing unit analyzes and compares the second phonetically oral cavity shape spectrum converted by the receiving-computing unit with the plurality of first phonetically oral cavity shape spectra stored in the database;
    wherein spectrum parameters of an audio transmitted by the transmitting module or received by the first receiving module is adjusted to allow the central computing unit correctly comparing and identifying one of the plurality of first phonetically oral cavity shape spectra stored in the database which is corresponds to the second phonetically oral cavity shape spectrum after the detecting signal generated by the transmitting module is received by the first receiving module.

2. The computer-aided conversion test system for generating intelligible speech as claimed in claim 1, wherein a third opening is disposed at another end of the laryngeal unit opposite to the end abutting the pharyngeal unit, and the third opening is disposed with a second receiving module connected to the receiving-computing unit.

3. The computer-aided conversion test system for generating intelligible speech as claimed in claim 2, wherein the second receiving module is adjusted to allow the central computing unit comparing and identifying one of the plurality of first phonetically oral cavity shape spectra stored in the database corresponding to and according to the second phonetically oral cavity shape spectrum after the detecting signal generated by the transmitting module is received by the second receiving module.

4. The computer-aided conversion test system for generating intelligible speech as claimed in claim 1, wherein the first receiving module is disposed at a position within 3 cm in front of the second opening of the oral cavity unit.

5. The computer-aided conversion test system for generating intelligible speech as claimed in claim 1, wherein the detecting signal is configured as a sound wave ranged from 16 Hz to 22 KHz.

6. A computer-aided conversion test method for generating intelligible speech, comprising following steps of:
- step S1: providing an acoustic test module with a nasal-genio-oropharyngeal tract, the nasal-genio-oropharyngeal tract including a nasal cavity unit with two first openings communicating with external environment, an oral cavity unit with a second opening communicating with external environment, a pharyngeal unit connecting the nasal cavity unit and the oral cavity unit, and a laryngeal unit abutting another end of the pharyngeal unit;
- step S2: providing a central processing module, the central processing module including a transmitting-computing unit, a receiving-computing unit, a database storing a plurality of first phonetically oral cavity shape spectra, and a central computing unit configured to perform machine learning;
- step S3: disposing a transmitting module at one of the first openings of the nasal cavity unit and a first receiving module at the second opening of the oral cavity unit respectively;
- step S4: generating a detecting signal by the transmitting module which is controlled by the transmitting-computing unit, and receiving the detecting signal reflected by the nasal-genio-oropharyngeal tract by the first receiving module;
- step S5: converting the detecting signal received by the first receiving module into a second phonetically oral cavity shape spectrum corresponding by the receiving-computing unit;
- step S6: analyzing the plurality of first phonetically oral cavity shape spectra and the second phonetically oral cavity shape spectrum by the central computing unit; and
- step S7: determining whether the transmitting module or the first receiving module require being adjusted, if the central computing unit correctly comparing and identifying one of the plurality of first phonetically oral cavity shape spectra stored in the database which corresponds to the second phonetically oral cavity shape spectrum, no adjustment being required, if the central computing unit being unable to correctly compare and identify one of the plurality of first phonetically oral cavity shape spectra stored in the database which corresponds to the second phonetically oral cavity shape spectrum, an adjustment being required, and step 4 is performed again.

7. The computer-aided conversion test method for generating intelligible speech as claimed in claim 6, wherein step S3 further includes disposing a second receiving module at a third opening at another end of the laryngeal unit opposite to the end abutting the pharyngeal unit.

8. The computer-aided conversion test method for generating intelligible speech as claimed in claim 6, wherein step S7 further includes adjusting the first receiving module to allow the central computing unit correctly comparing and identifying one of the plurality of first phonetically oral cavity shape spectra stored in the database which corresponds to the second phonetically oral cavity shape spectrum.

9. The computer-aided conversion test method for generating intelligible speech as claimed in claim 6, wherein in step S3, the first receiving module is disposed at a position within 3 cm in front of the second opening of the oral cavity unit.

10. The computer-aided conversion test method for generating intelligible speech as claimed in claim 6, wherein the detecting signal generated in step S4 is configured as a sound wave ranged from 16 Hz to 22 KHz.

* * * * *